United States Patent
Nardone et al.

(10) Patent No.: US 6,531,581 B1
(45) Date of Patent: Mar. 11, 2003

(54) PURINES AND PYRIMIDINES LINKED TO A QUENCHER

(75) Inventors: Glenn Nardone, Oakton, VA (US); Irena Nazarenko, Gaithersburg, MD (US); Jila Boal, McLean, VA (US)

(73) Assignee: Serologicals, Inc., Gaithersburg, MD (US)

( * ) Notice: Subject to any disclaimer, the term of this patent is extended or adjusted under 35 U.S.C. 154(b) by 0 days.

(21) Appl. No.: 09/646,669

(22) PCT Filed: Jun. 10, 1999

(86) PCT No.: PCT/US99/13107

§ 371 (c)(1),
(2), (4) Date: Oct. 26, 2000

(87) PCT Pub. No.: WO99/64431

PCT Pub. Date: Dec. 16, 1999

Related U.S. Application Data

(63) Continuation-in-part of application No. 09/095,014, filed on Jun. 10, 1998.

(51) Int. Cl.[7] .................. C07H 19/10; C07H 19/20; C07H 21/00

(52) U.S. Cl. ............... 534/560; 536/25.32; 536/26.6; 544/243; 544/244

(58) Field of Search ............... 544/243, 244; 534/560; 536/25.32, 26.6, 24.3

(56) References Cited

U.S. PATENT DOCUMENTS 5,047,519 A * 9/1991 Hobbs et al. .............. 536/23
6,117,986 A * 9/2000 Nardone et al. ........... 534/727

OTHER PUBLICATIONS

Aldrich Chemical Company, Milwaukee, WI, 1992, pp. 1077 and 1069.*
Fresenius, Philipp, "Organic Chemical Nomenclature", Halstead Press, Chichester, 1989, pp. 132–143.*
Hawley, Gessner, "The Condensed Chemical Dictionary", 1977, Van Nostrand, New York, pp. 626–627.*

* cited by examiner

Primary Examiner—Mukund J. Shah
Assistant Examiner—Thomas McKenzie
(74) Attorney, Agent, or Firm—Foley & Lardner

(57) ABSTRACT

Compounds are described comprising purines substituted at the C-8 position and pyrimidines substituted at the C-4 position with a linker and quencher. These compounds, when incorporated into hairpin oligonucleotides quench the fluorescence of fluorophores linked to the 5'-terminus of the oligonucleotide. These nucleotide-quencher compounds are also easily incorporated into oligonucleotides using conventional or automated oligonucleotide synthetic techniques.

20 Claims, 1 Drawing Sheet

PURINES AND PYRIMIDINES LINKED TO A QUENCHER

This application is the National Stage of PCT/US99/13107, which is a Continuation-In-Part of U.S. application Ser. No. 09/095,014, filed Jun. 10, 1998.

BACKGROUND OF THE INVENTION

Many procedures in medical research and recombinant DNA technology rely on the labeling of nucleotides that are then incorporated into oligo or polynucleotide probes. Commonly used labels have included radioactive isotopes, biotin, iminobiotin, haptens, fluorescent dyes and electron-dense reagents.

Problems with radioisotope labeling include the risk to the people handling the radioisotope-labeled material, and the need for elaborate and expensive safety precautions to be taken and maintained during the preparation, utilization and disposal of the radioactive material. Radioisotopes and radio-labeled nucleotides or polynucleotides are very expensive to purchase and use, due in part because of the safety precautions required and the problems in safely disposing of radioactive hazardous waste. In addition, the probe's structural integrity and sensitivity can be rapidly degraded during storage due to radioactive decay and radiochemical decomposition.

Oligo and polynucleotides can also be labeled with biotin and iminobiotin, haptens and fluorescent dyes for the direct detection of nucleotides. For example Ward et al. in U.S. Pat. Nos. 4,711,955; 5,449,767; 5,328,824; 5,476,928; herein incorporated by reference, describe the labeling of nucleotides with a hapten, biotin, or iminobiotin. The hapten is detected by a labeled antibody and the biotin or iminobiotin is detected by a labeled avidin or strepavidin.

Ruth, U.S. Pat. No. 4,948,882, herein incorporated by reference, describes the derivatization of nucleotides with fluorescent dyes, biotin, and antigens. Again, as in Ward et al. the biotin is detected by avidin, antigens are detected by labeled antibodies, and the fluorescent dyes are directly detected by spectral techniques.

The labeled nucleotides of Ruth are incorporated into oligo or polynucleotides by conventional phosphoramidite chemistry. The synthesized oligo or polynucleotides are then used as probes to detect DNA sequences. It is important to note that these labeled nucleotides are directly detectable when the probe is used in contrast to the labeled pyrimidines of the invention.

Labeling of nucleic acid probes with fluorophores facilitates microscopic analysis of chromosomes and their genetic structure by fluorescent in situ hybridization (FISH). A method of FISH probe preparation and signal detection is described by Ward et al. In the area of DNA diagnostics, automated platforms based on labeled synthetic oligonucleotides immobilized on silicon chips work by fluorescence detection and are capable of the parallel analysis of many samples and mutations. The methods used in preparing labeled, chemically activated nucleotide precursors for oligonucleotide synthesis is discussed and demonstrated by Ruth. Nucleic acid amplification methods such as PCR have become very important in genetic analysis and the detection of trace amounts of nucleic acid from pathogenic bacteria and viruses. Analysis of many PCR reactions by standard electrophoretic methods becomes tedious, time consuming and does not readily allow for rapid and automated data acquisition. PCR has been adapted to use fluorescent molecules by incorporation of fluorescent labeled primers or nucleotides into the product which is then directly detected or by the use of fluorescent probes that are then detected. Removal of unincorporated, labeled substrates is usually necessary and can be accomplished by filtration, electrophoretic gel purification or chromatographic methods. However, the large amount of sample handling required by these analytical techniques make these purification methods labor intensive, not quantitative and they invariably leads to serious contamination problems. Affinity capture of PCR products by strepavidin coated beads or micro titer wells requires incorporation of biotin labels in addition to the fluorophores and still involves transfer steps that can lead to contamination. Instrumentation utilizing both gel electrophoresis and laser excitation optics represents an improvement in data acquisition but cannot handle large numbers of samples, retains the comparatively prolonged separation times characteristic of gels and still requires sample transfer.

The use of fluorescent energy transfer, oligonucleotide primers containing hairpin secondary structure are described in U.S. Pat. No. 5,866,336, and in pending U.S. patent application Ser. Nos.: 08/837,034 filed Apr. 11, 1997 and 08/891,516 filed Jul. 11, 1997, each of which is entitled *Nucleic Acid Amplification of Oligonucleotides with Molecular Energy Transfer Labels and Methods Based Thereon*. The contents of all three of these documents are herein incorporated by reference. These documents solve the background problems associated with unincorporated, labeled substrates, alleviates sample transfer problems and enables the use of a homogeneous PCR assay for the analysis of many samples without cross contamination by amplicon. The unincorporated primer contains a target-specific, single stranded region with a 3'-hydroxyl terminus from which polymerase catalyzed elongation occurs. Under native conditions the unincorporated primer contains a tract of self complimentary nucleotides in the 5' region that are hydrogen bonded into a hairpin conformation. The 5'-hydroxy terminus is modified with a fluorophore. The 5'-deoxynucleotide is adenosine (dA). The last base of the double stranded hairpin stem region is a deoxyuridine (dU) which is base paired to the 5'-dA. The aromatic azo dye 4-dimethylaminoazobenzene-4'-sulfonyl chloride (dabsyl) is linked via a spacer arm to the C-5 carbon of the dU base. Hairpins can be extremely stable structures for their size, having high Tm's and strongly negative free energies. A hairpin is an intramolecular formation and is much more kinetically and entropically favored than the formation of a hybridized duplex. Under these structural conditions the fluorophore and the DABSYL are tightly held in close proximity to each other. At these short molecular distances the fluorophore and DABSYL can have orbital contact and overlap, being able to form relatively weak chemical interactions such as it complexes, hydrogen bonding or salt complex formation. This orbital interaction promote very efficient transfer of excitation energy from the fluor to the dabsyl. The DABSYL acceptor is not fluorescent and dissipates much of the donated or transferred energy as heat. While resonance energy transfer plays a role in the fluorescein or other fluorophore quenching other mechanisms of energy transfer can operate over these short distances as well and can account for the very efficient quenching of the fluor by the quencher.

After target hybridization and polymerase extension, the primer becomes a template for the next round of DNA replication. Polymerase displaces the 5'-end of the hairpin and copies the remainder. This process opens the hairpin conformation and the primer enters into the standard double helical B DNA conformation. The fluorophore and DAB- SYL are then separated by more than 60 Angstroms. The incorporated primer is now capable of producing strong fluorescent emissions when exposed to the appropriate excitation wavelengths. Unincorporated primer remains as a hairpin and produces very little flourescent emission for the reasons previously stated.

The hairpin, energy transfer primers are synthesized by standard automated phosphoramidite chemistry. See Caruthers, U.S. Pat. Nos.: 4,415,734 and 4,458,066 herein incorporated by reference. Linkage of the DABSYL moiety requires post synthetic modification. During oligonucleotide synthesis a commercially available dU phosphoramidite containing an aliphatic amino group linked to the base is incorporated. After deprotection and desalting the crude oligonucleotide is purified by reverse phase HPLC followed by solvent removal. The terminal amino group of the linker is reacted with a molar excess of commercially available dabsyl-succinimidyl ester or DABSYL sulfonyl chloride under alkaline conditions for 24 to 48 hours with the periodic addition of fresh, activated, dye during the incubation. The DABSYL modified oligonucleotide is precipitated and purified by reverse phase HPLC. After solvent removal the oligonucleotide is suspended in aqueous buffer, quantitated and tested. DABSYL coupling efficiencies are typically less than 80 percent and the entire process can take over a week to make preparative amounts of material. Final yields of product are typically much less than the coupling efficiency and are usually less than 50 percent. In addition, because the incorporation of DABSYL is not quantitative and the purification of DABSYL incorporated probes is not complete the probe is contaminated with oligonucleotide having a fluorescent molecule without a DABSYL quencher. Therefore probes having a quencher incorporated by this method will have a greater background fluorescence than probes made from the quencher linked pyrimidines of the invention.

SUMMARY OF THE INVENTION

The inventors have unexpectedly discovered that when mononucleotide precursors, in particular pyrimidines, are coupled to a quencher molecule and the quencher-pyrimidine is then incorporated into a probe using conventional phosphoramidite chemistry that the quencher-pyrimidine is stable during the protection and deprotection steps and is itself incorporated in good yield during the synthesis of hairpin, energy-transfer primers. The overall synthesis of the primers is also not effected by the quencher-pyrimidine nucleotide. The fluorophore will act as a fluorescence indicator when the hairpin is unfolded because the distance between the quencher and the fluorophore is greatly increased.

Compounds having the following general structure (A) are preferred:

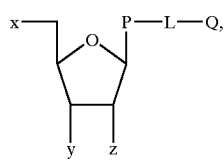

(A)

wherein L is a linker group, preferably comprising at least three carbon atoms, and Q is a quencher group; P is a pyrimidine group, preferably a uracil or cytosine group, and L is linked to the carbon atom at the 4 or 5 position of P, or P is a purine group, preferably an adenine group, and L is directly or indirectly linked to the carbon at the 8 position of P; and x is an activated phosphorous group capable of bonding to a 3' hydroxyl group of another nucleotide, y is a protected hydroxyl group, and z is —H, —F, —OCH$_3$, —O—allyl, a protected hydroxyl group, or a protected amine group, or y is an activated phosphorous group capable of bonding to a 5' hydroxyl group of another nucleotide, x is a protected hydroxyl group, and z is —H, —F, —OCH$_3$, —O—allyl, a protected hydroxyl group, or a protected amine group.

Preferably the linker has the following structure: —CH=CH—C(O)—NH—(CH$_2$)$_n$—NH—, —CH=CH—C(O)—NH—CH$_2$—CH$_2$—(O—CH$_2$—CH$_2$)$_m$—NH—, —C≡C—C(O)—(CH$_2$)$_n$—NH—, —CH=CH—C(O)—NH—(CH$_2$)$_n$—CO$_2$—, —CH=CH—C(O)—NH—(CH$_2$)$_n$—NH—, —(CH$_2$)$_n$—NH—, or —NH—(CH$_2$)$_n$—NH—, wherein n is an integer from 2 to 12, and m is 1 or 2. Most preferably, the linker has the following structure: —CH=CH—C(O)—NH—(CH$_2$)$_6$—NH—, —(CH$_2$)$_3$—NH—, or —NH—(CH$_2$)$_3$—NH—.

Q is a quencher capable of quenching the fluorescence of a flourescent dye when the quencher and dye are incorporated into a hairpin oligonucleotide. When the oligonucleotide is in the hairpin conformation the quencher is capable of substantially suppressing the fluorescence of the flourescent dye until the oligonucleotide is fully unfolded and is not in the hairpin conformation.

Preferably, x, y, and z each are —H, HO—, HO—P(=O)(—OH)—O—, HOP(=O)(—OH)—O—P(=O)(—OH)—O—, HOP(=O)(—OH)—O—P(=O)(—OH)—O—P(=O)(—OH)—O—, —OCH$_3$, —F, —NH$_2$, —O—allyl, benzyl, dimethoxytrityl, trityl, acetyl, phosphothioate such as is (HO)$_2$P(=S)—O— or (HO)$_2$—P(=O)—O—(HO)P(=O)—O—(HO)P(=S)—O—, methyl phosphoamidite, methyl Dhosphonoamidite, H-phosphonate, phosphotriester, —O-propargyl, silyl, and phosphoamidite such as ((CH$_3$)$_2$CH)$_2$—N—P(OCH$_2$CH$_2$CN)—O— or ((CH$_3$)$_2$CH)$_2$—N—P(OCH$_3$)—O—, or bonded to a support such as —O—C(O)—(CH$_2$)$_2$—C(O)-alkylamino-support.

The quencher is preferably a non-fluorescent dye, e.g., acid alizarin violet N, acid black 24, acid blue 29, acid blue 92, acid blue 113, acid blue 120, and blue 161, acid orange 8, acid orange 51, acid orange 74, acid red 1, acid red 4, acid red 8, acid red 37, acid red 40, acid red 88, acid red 97, acid red 106, acid red 151, acid red 183, acid violet 7, acid yellow 17, acid yellow 25, acid yellow 29, acid yellow 34, acid yellow 38, acid yellow 40, acid yellow 42, acid yellow 65, acid yellow 76, acid yellow 99, alizarin yellow 66, crocein orange G, alizarin blue black B, palatine chrome black 6BN, mordant black 3, basic red 29, basic blue 66, brilliant yellow chrysophine, chrysoldin, crocein orange G, crystal scarlet, fast black K salt, fast corinth V salt, fast garnet GBC, fat brown B, fat brown RR, mordant blue 9, mordant brown 1, mordant brown 4, mordant brown 6, mordant brown 24, mordant brown 33, mordant brown 48, mordant orange 1, mordant orange 6, mordant orange 10, oil red E6N, oil red O, orange 11, orange G, palatine chrome black 6BN, palatine fast yellow BLN, tropaeolin O, acid yellow 36, 4-dimethylamino-2-methylazobenzene, disperse orange 1, disperse orange 3, disperse orange 13, disperse orange 25, disperse red 1, disperse red 13, disperse red 19, disperse yellow 3, disperse yellow 5, disperse yellow 7, ethyl red, methyl red, napthyl red, 4-phenylazoaniline, 4-phenylazomalcinanil, 4-phenylazophenol, 4(4-nitrophenolazo)resorcinol, nitro red, orange II, para red, Sudan I, Sudan II, Sudan III, Sudan IV, Sudan Orange G, or Sudan Red 7B; or a non-fluorescent triphenyl methane dye, e.g., alkali blue 6B, aniline blue, aurintricarboxylic acid, basic violet 14, basic red 9, brilliant green, bromochlorophenol blue, bromocresol purple, chlorophenol red, crystal violet, ethyl violet, fast green FCF, guinea green B, malachite green, methyl green, new fuchsia, pyrocatechol violet, thymol blue, thymolphthalin, Victoria blue B, victoria blue R, or victoria pure blue BO. Preferably, the non-fluorescent triphenyl methane dye contains an isocyanate group, an isothiocyanate group, or an N-succinimidyl ester group. If the quencher is malachite green, it preferably contains an amine group bonded to the atom at the 4 position. Other preferred quenchers are uniblue B, alizarin blue black B, alizarin red S, alizarin violet 3R, fast blue BB, and fast blue RR.

Ideally, the quencher has the following general structure (B):

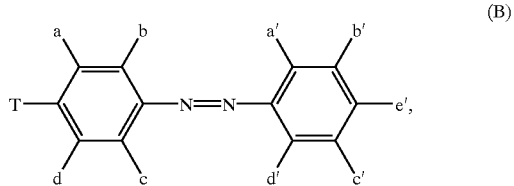

wherein T is —NH—, —SO$_2$—, —O—, —S—, —C(O)—S—, —C(O)—, —C(O)—NH—, —C(O)—O—, —C(S)—NH—, or —C(S)—O—; a, a', b, b', c, c', d, d', and e' are each —H, —Cl, —Br, —F, —OCH$_3$, —OH, —CH$_3$, —SO$_3$—, diazophenyl, diazo-1-naphthyl, —CO$_2$R, or —N(R)$_2$; and R is —H, —CH$_3$, —CH$_2$—CH$_3$, or O.

The invention is also directed to a method for producing a compound containing at least two nucleotide groups, e.g., an oligonucleotide, wherein the method comprises linking the compound of claim 1 to another compound containing at least one nucleotide or nucleotide group.

The compounds of the invention can be readily prepared by the following process:

(a) reacting a pyrimidine nucleotide with a mercuric salt in a suitable solvent under suitable condition so as to form a pyrimidine mercurated at the C-5 position;

(b) reacting said mercurated pyrimidine with a linker having a reactive terminal double or triple bond to react with the -Hg portion of the pyrimidine compound in the presence of K$_2$PdCl$_4$ in an aqueous solvent and under suitable conditions so as to form the linker-pyrimidine compound.

(c) reacting the Pyr-L-NH$_2$ with a quencher, selected from non-fluorescent azo dyes and non-fluorescent triphenyl methane dyes and other suitable compounds having at least one moiety capable of reacting with the amino functionality of the Pyr-L-NH$_2$ preferably with a quencher having a sulfonyl chloride, carboxylic acid chloride, N-succinimidyl ester, isocyanate or isothiocyanate. Alternatively the terminal —NH$_2$ group of the linker is activated by forming an isocyanate or isothiocyanate and then reacting the isocyanate or isothiocyanate with an alcohol or amino moiety on the dye to form the desired pyrimidine-quencher compound.

The P-L-quencher described above is then used in the preparation of primers. The P-L-quencher are readily incorporated into the growing oligonucleotide during its synthesis using automated oligonucleotide techniques and equipment. It was also discovered that DABSYL was a preferred quencher. However, DABSYL or other quenchers are not available in the form of dabsyl-nucleotide phosphoamidites. Consequently, a deoxyuridine β-cyanoethyl phosphoramidite containing a DABSYL moiety linked to the base via a linker arm (dU-dabsyl) was prepared as described in the present application. A number of hairpin primers incorporating a pyrimidine-quencher were synthesized on an automatic DNA synthesizer. Analytical HPLC revealed an increase in primer yields to between 80 to 90%, indicating surprisingly efficient coupling of the dU-DABSYL and stability of the dU-DABSYL through many synthetic cycles. Analysis of the fluorescent properties of these primers revealed unexpectedly high signal to noise ratios in samples that had only been desalted and not purified by HPLC. The enhanced signal to noise in impure samples may be due to the incorporation of the DABSYL before the addition of the fluorophore because the synthesis of oligonucleotides occur in the 3' to 5' direction. Consequently, even the most efficient synthesis will have a slight excess of oligonucleotides containing DABSYL with no fluorophore. When the DABSYL is not incorporated into the primer the fluorophore is not quenched when the primer is in the hairpin conformation. This situation is far more likely to occur with the post synthetic modification of the primer using activated dye since the reaction with the amine typically has an efficiency less than 80 percent. An unexpected advantage of incorporation of the quencher molecule by means of a dU-quencher in the probe synthesis is that the probe will have a statistically greater change of having a quencher molecule than a fluorescent dye molecule so that the background fluorescence of the probe is substantially reduced.

DETAILED DESCRIPTION OF THE INVENTION

Figure 1:
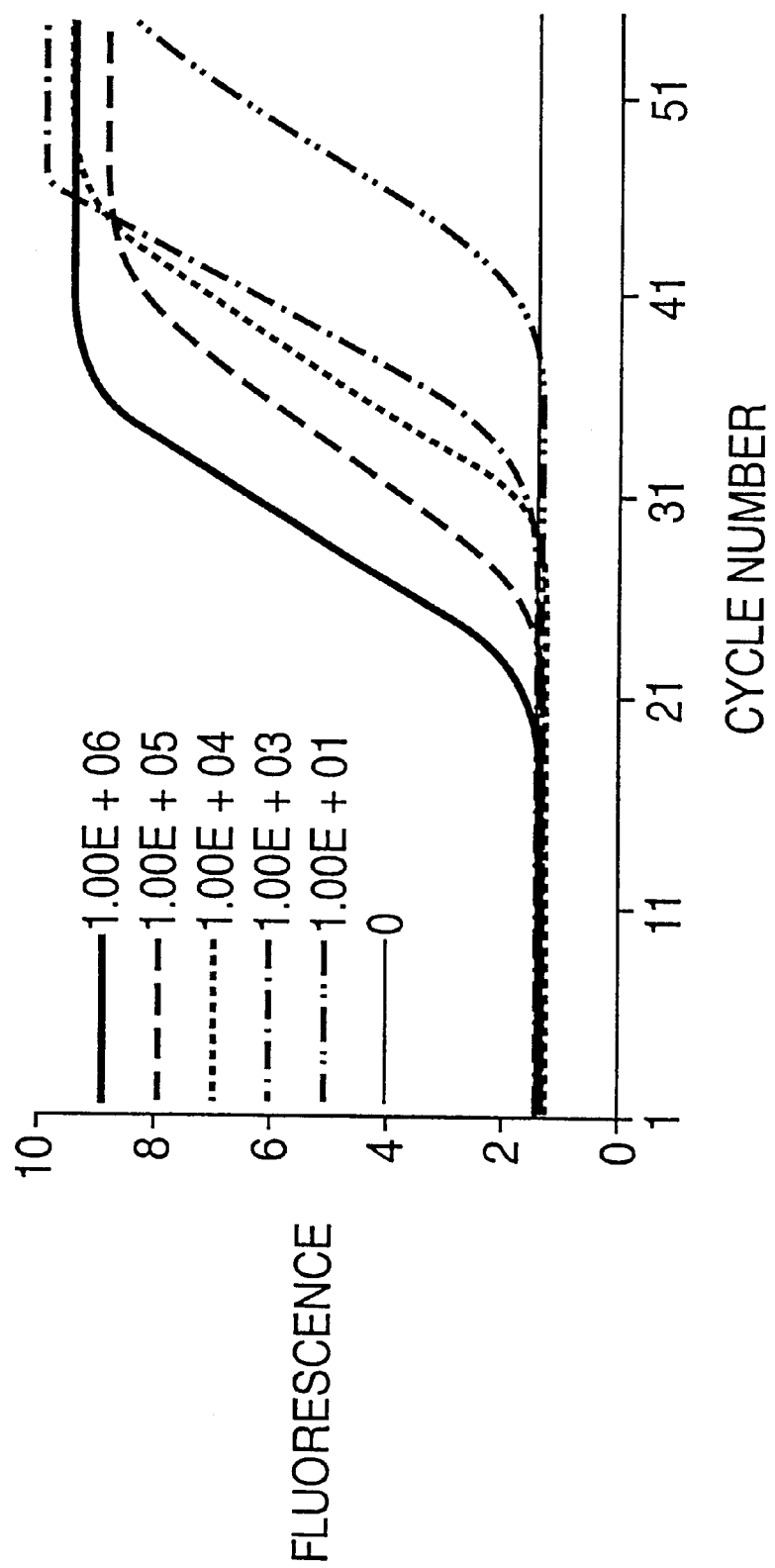
FIG. 1 is a graph plotting fluorescence versus the number of PCR cycles for differing concentrations of recombinant HIV 1 DNA.

The present invention provides a quencher moiety attached by a linker arm to a purine or pyrimidine nucleotide having the following structure (A):

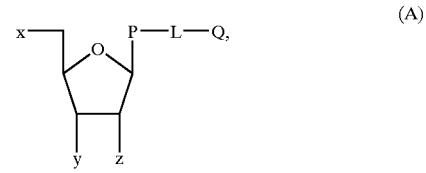

The quencher-linker-P nucleotide can be readily incorporated into oligonucleotides using conventional solid phase oligonucleotide synthetic techniques described by *Caruthers* et al. in U.S. Pat. Nos. 4,415,734 and 4,458,066 or by techniques of *Letsinger* et al. J. Org. Chem. vol. 45, 2715 (1980) and reviewed by *Matteuci* et al. J. Amer. Chem. Soc.: vol. 103 p. 3185 (1982) both articles herein incorporated by reference. Preferred oligonucleotides with the quencher-P are hairpin probes with a flourescent dye at the 5'-end of the oligonucleotide as described in *Nucleic Acid Amplification of Oligonucleotides with Molecular Energy Transfer Labels and Methods Based*, U.S. Pat. No. 5,866,336. When the oligonucleotide in the hairpin configuration the quencher and the flourescent dye are in close proximity to each other so that the quencher will quench the fluorescence of the fluorescent dye and when the oligonucleotide is in the linear configuration the quencher and fluorescent dye are far enough apart so that the quencher no longer quenches the fluorescence of the fluorescent dye. Although any compound that will quench the fluorescence as described above are suitable, preferred quenchers are non-fluorescent azo dyes, non-fluorescent triphenyl methane dyes, and dyes such as Uniblue-B. The dyes should be non-fluorescent because an acceptor fluorescent dye can have fluorescent emissions that will spill into assay wavelengths and increase the background noise. Furthermore, emissions from fluorescent quenchers can interfere with applications involving several different assay fluorophores having different colors. Examples of such applications would include multiplex PCR and fluorescent internal controls. Preferred non-flourescent azo dyes have the following structure (B):

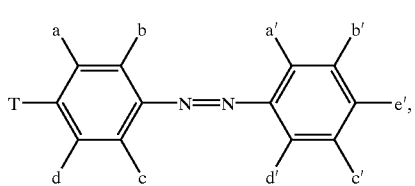

(B)

wherein: T is independently selected from —NH—, —SO$_2$—, —O—, —S—, —(CO)—S—, —C(O), C(O)—NH—, —C(O)—O—, —C(S)—NH— and —C(S)—O—; a, a', b, b', c, c', d, d' and e' are independently selected from H, Cl, Br, F, —OCH$_3$, —OH, —CH$_3$, —SO$_3$—, diazophenyl, diazo-1-naphthyl, —CO$_2$R and N(R)$_2$ and R is independently selected from H, —CH$_3$, —CH$_2$—, —CH$_3$ and O.

Particularly preferred compounds are those where e' is —N(R)$_2$ and R is independently selected from H, —CH$_3$ and —CH$_2$CH$_3$. Even more preferred are nonflourescent azo dyes when a, a', b, b', c, c', d and d' are H, and e' is N(R)$_2$ wherein R is —CH$_3$ or —CH$_2$CH$_3$, and T is SO$_2$.

Examples of non-fluorescent azo dyes which may be used according to the invention are as follows: acid alizarin violet N, acid black 24, acid blue 29, acid blue 92, acid blue 113, acid blue 120, acid blue 161, acid orange 8, acid orange 51, acid orange 74, acid red 1, acid red 4, acid red 8, acid red 37, acid red 40, acid red 88, acid red 97, acid red 106, acid red 151, acid red 183, acid violet 5, acid violet 7, acid yellow 17, acid yellow 25, acid yellow 29, acid yellow 34, acid yellow 38, acid yellow 40, acid yellow 42, acid yellow 65, acid yellow 76, acid yellow 99, alizarin yellow 66, alizarin blue, black B, palatine chrome black 6BN, mordant black 3, basic red 29, basic blue 66, brilliant yellow chrysophenine, chrysoldin, crocein orange G, crystal scarlet, fast black K salt, fast corinth V salt, fast garnet GBC, fat brown B, fat brown RR, mordant blue 9, mordant brown 1, mordant brown 4, mordant brown 6, mordant brown 24, mordant brown 33, mordant brown 48, mordant orange 1, mordant orange 6, mordant orange 10, oil red E6N, oil red O, orange 11, orange G, palatine chrome black 6BN, palatine fast yellow BLN and topaeolin O. Particularly preferred non-flourescent azo dyes include acid aldzarin violet N, acid black 24, acid blue 92, acid blue 113, acid blue 120, acid orange 8, acid orange 51, acid orange 74, acid red 1, acid red 4, acid red 8, acid red 37, acid red 88, acid red 151, acid red 183, acid yellow 34, acid yellow 40, acid yellow 76, crocein orange G, crystal scarlet, mordant blue 9, mordant brown 1, mordant brown 33, mordant orange 1, mordant orange 6, mordant orange 10, orange 11, orange G, palatine chrome black 6BN, palatine fast yellow BLN and topaeolin O.

Examples of non-fluorescent triphenyl methane dyes which can be used according to the invention are selected from: alkali blue 6B, aniline blue, aurintricarboxylic acid, basic violet 14, basic red 9, brilliant green, bromochlorophenol blue, bromocresol purple, chlorophenol red, m-cresol purple, cresol red, crystal violet, ethyl violet, fast green FCF, guinea green B, malachite green, methyl green, new fuschia, pyrocatechol violet, thymol blue, thymolphthalein, victoria blue B, victoria blue R and victoria pure blue, both as the isocyanate or isothiocyanate derivatives. A preferred non-fluorescent triphenyl methane dye is malachite green derivatized at the 4 position of the phenyl ring with isothiocyanate. Other non-fluorescent dyes that can be used as a quencher include alizarin blue black B, alizarin red S, alizarin violet 3R, fast blue BB, and fast blue RR.

It should be noted that when the nucleotide incorporating the non-fluorescent dye is incorporated into a hairpin probe as previously described, the concentration of the hairpin probe in an assay system is such that the non-fluorescent dye is not detectable by a spectrophotometer.

Examples of pyrimidines which can be used are uridine, thymadine, and cytosine. Uridine is preferred.

The linker, L, comprises at least three carbon atoms and links the pyrimidine with the quencher moieties. Preferred examples of the linker, L, which can be used in the invention are:

—CH=CH—C(O)—NH—(CH$_2$)$_n$—NH—;

—CH=CH—C(O)—NH—CH$_2$—CH$_2$—(O—CH$_2$—CH$_2$)$_m$—NH—;

—C≡C—C(O)—(CH$_2$)$_n$—NH—;

—CH=CH—C(O)—NH—(CH$_2$)$_n$—CO$_2$— and n is 2–12 and m is 1, 2 or 3.

The preferred linkers are —CH=CH—C(O)—NH—(CH$_2$)$_n$—NH— and —CH=CH—C(O)—NH—CH$_2$—CH$_2$—(O—CH$_2$—CH$_2$)$_m$—NH— and n is 2–12 and m is 1, 2 or 3. *M. Pearlman* et. al. in J. Medicinal Chemistry vol. 28 pp 741–748 (1985) herein incorporated by reference, describe techniques for forming 5-substituted pyrimidines including 2'-deoxycytidine derivatives and terminal acetylene derived linker arm compounds.

Each of x, y and z are selected as follows: whenever x is an activated phosphorus group capable of intermolecular bond formation with a 3' hydroxyl of another nucleotide, then y is a protected hydroxyl group and z is —H, —F, —OCH$_3$, —O-allyl or a protected hydroxyl or amine group and whenever y is an activated phosphorus group capable of intermolecular bond formation with a 5' hydroxyl of another nucleotide then x is a protected hydroxyl group and z is —H, —F, —OCH$_3$, —O-allyl or a protected hydroxyl or amine group. Preferred x, y and z's are selected from —H, HO—, HO—P(=O)(—OH)—O—, HOP(=O)(—OH)—O—P(=O)(—OH)—O—, HOP(=O)(—OH)—O—P(=O)(—OH)—O—P(=O)(—OH)—O—, —OCH$_3$, —F, —NH$_2$, —O-allyl, benzyl, dimethoxytrityl, trityl, acetyl, phosphothioates such as (HO)$_2$P(=S)—O—, (HO)$_2$P(=O)—O—(HO)P(=O)—O—(HO)P(=S)—O—, methyl phosphoamidite, methyl phosphonoamidite, H-phosphonate, phosphotriesters, —O-propargyl, silyls, support bound such as —O—C(O)—(CH$_2$)$_2$—C(O)—alkylamino-support, and phosphoamidites such as ((CH$_3$)$_2$CH)$_2$—N—P(OCH$_2$CH$_2$CN)—O—, ((CH$_3$)$_2$CH)$_2$—N—P(OCH$_3$)—O—. More preferred z is H and even more preferred x is dimethoxytrityl, y is ((CH$_3$)$_2$CH)$_2$—N—P(—OCH$_2$CH,CN)—O— and z is H.

In a preferred embodiment of the present invention, when the protective group for hydroxyl compounds is a —O-silyl group, the silyl group is selected from the group consisting of trimethylsilyl, triisopropylsilyl and t-butyldimethylsilyl.

The compounds of the invention are readily synthesized by the following procedure.

(a) Reacting the pyrimidine, preferably uridine with a mercuric salt in a suitable, preferably aqueous, solvent under suitable conditions so as to form a uridine mercurated at the C-5 position;

(b) reacting the mercurated uridine with the terminal double or triple bond of a linker moiety represented by the linker formulas:

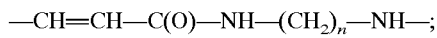

—CH═CH—C(O)—NH—CH$_2$—CH$_2$—(O—CH$_2$—CH$_2$)$_m$—NH—;

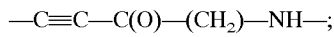

—CH═CH—C(O)—NH—(CH$_2$)$_n$—CO$_2$— and wherein n is 2–12 and m is 1, 2 or 3 with LiPdCl$_3$ to form uridine-linker having the following general formula (C):

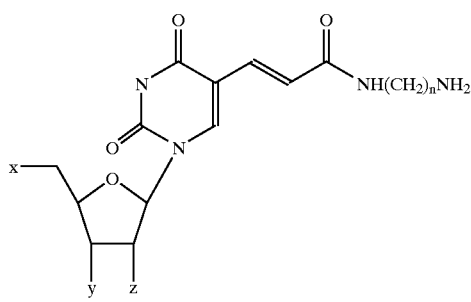

(c) allowing the —NH$_2$ of the linker moiety to react with a quencher molecule to form the uridine-quencher molecule (D).

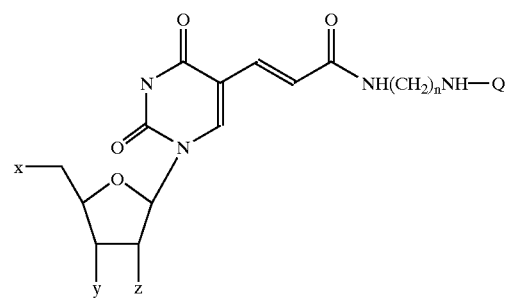

The quencher molecule may have a sulfonic acid or carboxylic acid moiety which is derivatized to the corresponding acid chloride. The acid chloride moiety of the quencher molecule is allowed to react with the amino moiety of the linker group to form the corresponding amide.

Alternatively, the quencher molecule may have an amine or hydroxy moiety which is attached to the amine group of the linker arm by either derivatizing the amine group of the linker to form an isocyanate or isothiocyanate and then allowing the isocyanate or isothiocyanate group of the linker to react with the amine or hydroxyl group of the quencher molecule to form the respective urea or thiourea and carbamate or thiocarbamate groups. The amine group of the quencher can also be derivatized to form the isocyanate or isothiocyanate and allowed to react with the amine group of the linker to again form the urea or thiourea link. The hydroxy group can be derivatized to form the chlorocarbonate which is allowed to react with the amine group to form the respective carbamate. When the terminal group of the linker is a carboxylic acid the carboxylic acid can be reacted with alcohols or amines on the quencher to form the respective esters and amides with the quencher.

Alternatively, when the quencher has an aldehyde moiety the amine of the linker group can be allowed to react with the aldehyde, followed by reduction of the imine with sodium cyanoborohydride or other reducing agents to form an amine linkage.

Another, alternative method of making the quencher-pyrimidines of the invention is to react the amine functionality of the linker group with the quencher before the linker arm is attached to the nucleotide to form a linker-quencher. This reaction between the linker and quencher can be accomplished by a variety of different, conventional, organic reactions such as the reaction of acid chlorides or acid anhydrides with amines to form amides. The reactions can include, depending on the terminal group of the linker and the quencher, the reaction of a sulfonyl chloride with an amine to form a sulfonamide, the reaction of an isocyanate with an amine or alcohol to form a urea or a carbamate respectively, the reaction of an isothiocyanate with an amine or alcohol to form a thiourea or thiocarbamate respectively or the reaction of an activated carboxylic acid with an alcohol or amine to form an ester or amide, respectively.

Once formed, the nucleotides-quencher molecules of the invention can be readily incorporated into oligo and polynucleotides using conventional phosphoramidite chemistry. When the nucleotide-quencher molecules of the invention are incorporated into the hairpin oligonucleotides described in U.S. Pat. No. 5,866,336, the quencher molecule, even though it is a dye molecule as described in this application, is undetectable spectrophotometrically, when the probes are used at a concentration suitable for polynucleotide amplification.

The following examples are included to aid those skilled in the art to practice the invention. The examples should not be considered limitations upon the scope of the claimed invention but merely being illustrative thereof.

EXAMPLE 1

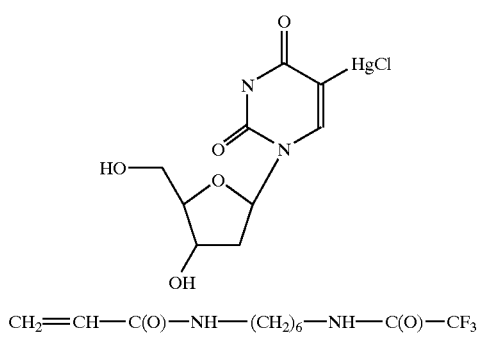

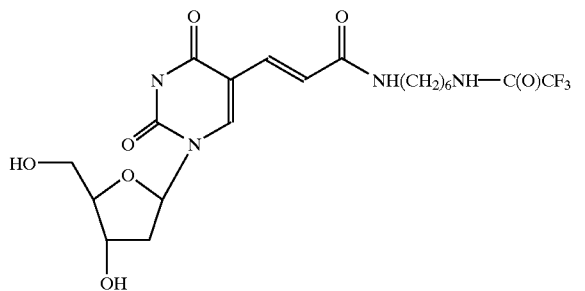

1.67 gm of linker (II) in 12.6 ml of CH$_3$CN is added to a 100 ml round bottom flask equipped with a stir bar. 50 ml of 0.2N LiPlCl$_3$ in CH$_3$CN is added and the mixture is heated to 50–60° C. for 15–20 minutes, then 2.24 gm of 5-HgCl-dUrd (I) is added. The solution is stirred under reflux for six hours. The mixture is then allowed to cool and H$_2$S is bubbled through the mixture for 10 minutes. The mixture is filtered through Celite®. The black catalyst is washed with warm methanol and the methanol and acetonitrile solutions are combined and the solvent is removed by evaporation. 5 grams of crude residue was recovered. The crude product is purified on a silica gel column using CHCl$_3$: MeOH (85:15) as the eluant. 1.4 grams of product (III) was recovered.

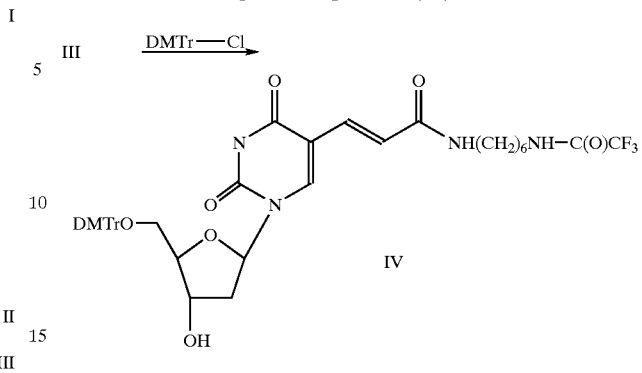

Co-evaporate 492 mg (0.001 mol) of derivative III three times with 15 ml of anhydrous pyridine, then dissolve the solid in a further 10 ml of anhydrous pyridine. Then add 339 mg (0.001 mole), one equivalent of DMTrCl and allow the mixture to react under observation. After 1 hour, an additional 68 mg (0.2 equivalent) DMTrCl was added with stirring. After a further hour 4 or 5 additions of a further 68 mg DMTrCl was added until the reaction was complete. 10 ml of methanol was then added to destroy the excess DMTrCl and the solution was allowed to stir for 15 minutes.

The solvents were then evaporated using a rotary evaporator and water driven vacuum pump. The residue was washed with 10 ml of cold water then dissolved with two 15 ml aliquot of methylene chloride. The methylene chloride aliquots were combined, dried and the methylene chloride removed to yield 700 mg of a crude product. The crude reaction mixture was purified by passing it through a silica gel flash chromatography column using CHCl$_3$-MeOH (93-7) as the eluant. 400 mg of pure tritylated material was recovered. The trifluoroacetyl protecting group (TFA) was removed by dissolving 1.9 gm of trityl derivative in 19 ml of a 2M methylamine in MeOH solution. The reaction vessel is tightly stoppered and heated in an oil bath at 40° C. overnight after which the TFA deprotection is complete.

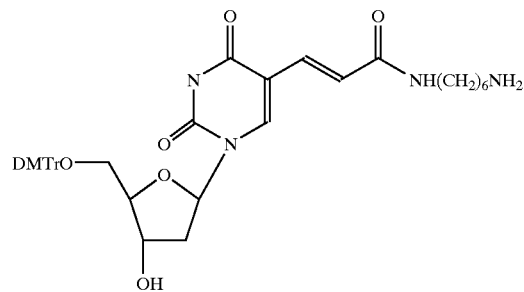

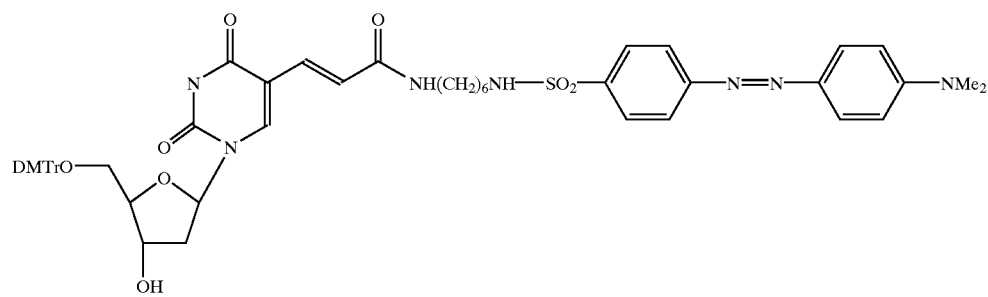

Dissolve 140 mg of deprotected 5'-DMTr-aminolinked dU (V) (0.0002 moles) in 0.3 ml of dry DMF. Placed the round bottom flask in an ice bath, add 0.002 mole (279 µl) NEt$_3$ and stir. Dissolve 648 mg, 10 equivalents, (0.002 mole) DABSYL chloride in 2 ml dry DMF and add the solution, dropwise to the chilled solution of V and NEt$_3$. Remove the ice bath and allow the solution while stirring to warm to room temperature then continue stirring for three hours. After stirring evaporate the DMF with a rotary evaporator with the vacuum provided by an oil vacuum pump at 40° C. Purify the product by chromatography on a silica gel column using CH$_2$Cl$_2$: MeOH (97:3) then CH$_2$Cl$_2$: MeOH (93:7) to recover 100 mg of the pure dU-DABSYL derivative VI.

To a round-bottom flask which is fitted with a reflux condensor and magnetic stirrer containing the compound of Formula (C) (1 eq.), 2 eq. of phosphorus pentachloride in solution is added drop-wise. The reaction mixture is heated and upon completion of the reaction, the reaction mix is poured over ice, the product is collected by suction filtration. The dry product is washed with acetone in an extractor.

The ethyl orange can also be derivatized by reaction with thionyl chloride as follows. To a round bottom flask fitted with a reflux condensor and a magnetic stirrer containing 1 eq. of ethyl orange is added 5 eq. of thionyl chloride drop-wise. The reaction mixture is heated and stirred until the reaction is complete. Excess thionyl chloride is driven

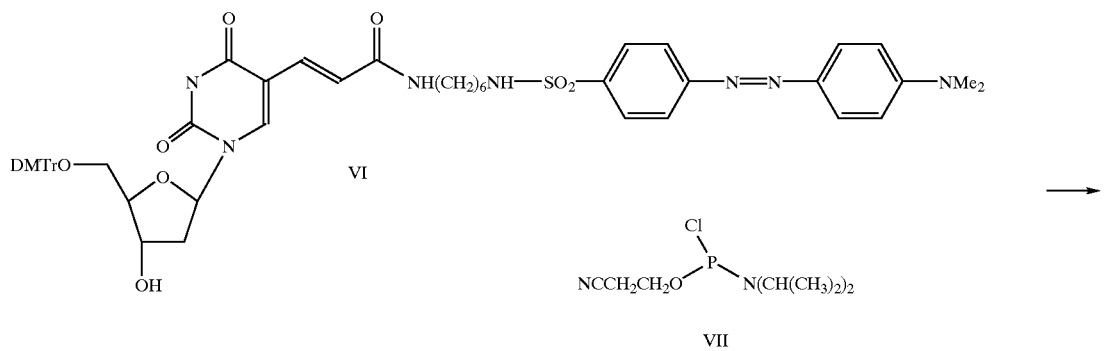

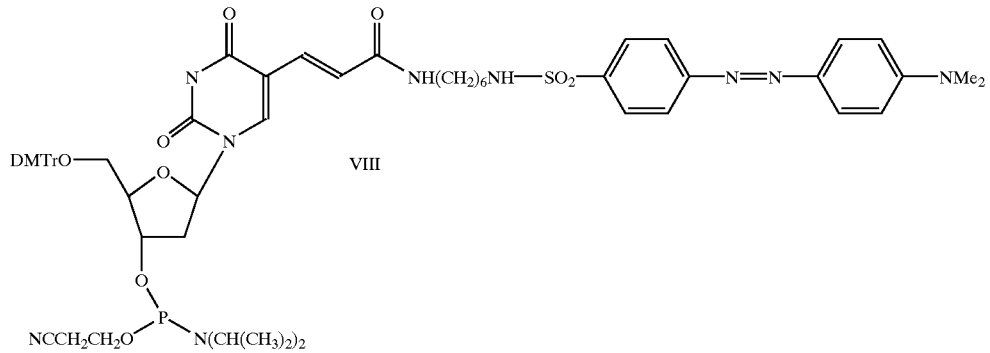

Co-evaporate 100 mg (0.0001 mole) of VI three times with 15 ml anhydrous CH$_3$CN and then dry over P$_2$O$_5$ under vacuum from a vacuum pump overnight. In a 25 ml round bottom flask, 100 mg of VI is dissolved in 3 ml dry CH$_2$Cl$_2$ and 3 equivalents, 0.03 gm, 40 µl NEt$_3$. Then rapidly add 1.2 equivalents, 0.028 gm 27 µl of 2-cyanoethyl diisopropylchloro-phosphoramidite VII in a dropwise manner. Stir for 45 minutes, and because the reaction is partial add another 1.2 equivalents, 27 µl phosphoramidite VII and stir for an additional 45 minutes at which point the reaction is almost complete. Add 20 ml of CH$_2$Cl$_2$ wash with 5% aqueous NaHCO$_3$, dry the CH$_2$Cl$_2$ with Na$_2$SO$_4$ and evaporate the CH$_2$Cl$_2$ to recover 120 mg of crude product VIII. Purify the crude product by passing it through a silica gel flash column using EtOAc: triethylamine 95:5 to recover 110 mg of pure phosphoramidite VIII.

Alternatively, derivatized ethyl orange can be added to the pyrimidine-nucleotide to which the linker has been incorporated in place of the DABSYL chloride. In order to react the ethyl orange with a compound of Formula (C), ethyl orange is derivatized to the corresponding sulfonyl chloride.

off by distillation under reduced pressure and the derivatized product is recovered.

In another embodiment, naphthyl red, fast garnet GBC or 4-phenylazoaniline can be used in place of the DABSYL chloride. To derivatize one of the above dyes to the sulfonyl chloride, sodium nitrite is added in excess with concentrated HCl in an ice bath (0° C.) to the dye to yield a non-isolated intermediate of a diazonoium salt of the dye. The intermediate is subsequently reacted with SO$_2$, CuCl$_2$ and KCl in a suitable solvent system, e.g., a 1:1 mixture of benzene and dioxane. The mixture is heated to about 50° C., for about at least 30 minutes. Then the reaction is quenched with the addition of water, and the product is extracted with a solvent. The product is then washed with an aqueous solution of NaOH, extracted again with a suitable solvent and then the solvent is removed by, e.g., rotary evaporator and dried over, e.g., Celite®.

In a further embodiment, fast corinth V can be used in place of DABSYL chloride, but is derivatized to its sulfonyl chloride prior to incorporation in the pyrimidine-nucleoside. Fast corinth V has the following structure:

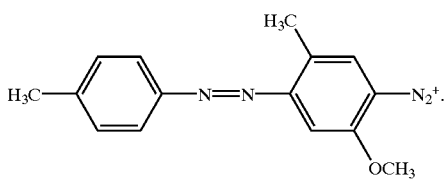

Fast corinth V is reacted with $SO_2$, $CuCl_2$ and KCl in a suitable solvent system, e.g., a 1:1 mixture of benzene and dioxane. The mixture is heated to about 50° C., for about at least 30 minutes. Then the reaction is quenched by the addition of water, and the product is extracted with a solvent. The product is then washed with an aqueous solution of NaOH, extracted again with a suitable solvent and then the solvent is removed by, e.g., rotary evaporator and dried over a drying agent, e.g., Celite®.

Even though the previous examples utilize a sulfonyl chloride for the incorporation of the Q group to the pyrimidine-nucleoside-linker, other reactive functional moieties may be used.

For example, dyes such as naphthyl red, fast garnet and 4-phenylazoaniline can be derivatized to their corresponding isothiocyanates or succinimidyl esters as detailed below.

The isothiocyanate of any of the above dyes is prepared by combining the dye with an excess of thiocarbonyldiimidazole to yield the isothiocyanate of the dye. For example, the isothiocyanates of naphthyl red, fast garnet GBC and 4-phenylazoaniline are as follows:

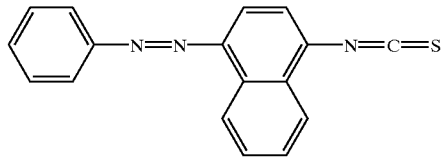

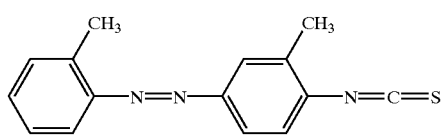

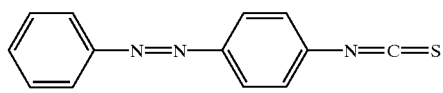

Alternatively, the isothiocyanates can be prepared by reacting the dye with thiophosgene with a solvent, such as pyridine or triethylamine with heating from 0° to 50° C. The excess reagent is removed by distillation under reduced pressure and the product is then recovered.

The succinimidyl esters, such as the succinimidyl ester of ethyl red, is prepared by reacting the dye with N-hydroxysuccinimide and DCC (dicyclohexylcarbodiimide) in a DMF (dimethylformamide) solvent system at about 0° for about 10 to 20 hours. Upon completion of the reaction, the product mixture is dried under a high vacuum, re-suspended in an acetic acid-methanol solvent system. The product is precipitated out, washed, re-dissolved and dried to yield the succinimidyl ester product.

EXAMPLE 2

A number of different fluorophores were incorporated into DABSYL derivatized hairpin probes in a manner more fully described in *Nucleic Acid Amplificaion Oligonucdeotides with Molecular Energy Transfer Labels and Methods Based Thereupon*. The quenching data shown in Table 1 was obtained using the identified fluorophores in a hairpin probe.

TABLE 1

| Fluorophore | Excitation/Emission (nm) | Fold Quench |
|---|---|---|
| AMCA | 353/450 | 15 |
| Fluorescein | 495/516 | 52 |
| JOE | 535/555 | 50 |
| TAMRA | 560/584 | 37 |
| Bodipy 564 | 580/590 | 15 |
| ROX | 594/616 | 23 |
| Texas Red | 595/620 | 18 |

However, the structure and sequence of the oligonucleotide can have large effects on the quench values.

EXAMPLE 3

Oligonucleotides containing a dU linked amino group, similar to V of Example 1, were derivatized with malachite green isothiocyanate and purified by HPLC. Fluorescence assays using oligonucleotides similar to the oligonucleotides of Example 2 were performed and the results shown in Table 2 were obtained:

TABLE 2

| Fluorophore | Excitation/Emission (nm) | Fold Quench |
|---|---|---|
| TAMRA | 560/584 | 3.0 |
| ROX | 594/616 | 3.5 |
| Bodipy 581 | 590/605 | 4.0 |
| Texas Red | 595/620 | 5.0 |

Again, the structure and sequence of the oligonucleotides can have large effects on the quench values.

EXAMPLE 4

Use of Oligonucleotides with Incorporated dU-DABSYL Phosphoramidites as PCR Primers to Detect HIV-1 Virus in Real Time The following oligonucleotide primers were chemically synthesized and purified:

BSK 38 was synthesized using phosphoramidite chemistry with standard cycles at 0.2 μmol scale on an Applied Biosystems-PE 394 synthesizer. The oligonucleotide was cleaved from the support and deprotected in ammonium hydroxide at 55° C. for 10 hours. Ammonium hydroxide and low molecular weight contaminants were removed by gel filtration chromatography on Sephadex G-25. The column was equilibrated and eluted with deionized water. The primer was quantitated by UV spectroscopy at 260 nm and has the following sequence: d(ATAATCCACCCTATCC CAGTAGGAGAAAT) (SEQ ID NO: 1).

BSK 39 was synthesized by phosphoramidite chemistry on an Applied Biosystems-PE 394 synthesizer at a 1.0 μmol scale. Standard base coupling steps and acetylation times were extended to one minute and 10 seconds respectively. Prior to synthesis 50 μmol of dry dU-DABSYL phosphoramidite was dissolved in anhydrous acetonitrile at a concentration of 100 mM. At the appropriate step the dU DABSYL was allowed to couple for ten minutes. The 5' terminus of the oligonucleotide was labeled by the addition of a fluorescein phosphoramidite at the terminal step. The oligonucleotide was deprotected at room temperature for 24 hours in ammonium hydroxide. Ammonium hydroxide and low molecular weight contaminants were removed by gel filtration chromatography on Sephadex G-25. The column was equilibrated and eluted with deionized water. The oligonucleotide was further purified by reverse phase HPLC. After solvent removal the oligonucleotide was dissolved in deionized water and quantitated by UV spectrophotometry. The signal to noise values were determined in a Shimadzu spectrofluorimeter using excitation and emission wavelengths of 495 and 516 nm respectively. The fluorescence of 5 pmol of oligonucleotide was determined in 0.6 ml of 10 mM Tris-HCl pH 8.0, 2 mM $MgCl_2$, 50 mM NaCl or 15 mM NaOH. A 30-fold difference in fluorescence was observed between reading taken in neutral buffers (hairpin conformation) and alkaline solutions (linear conformations). Over a 20-fold increase in fluorescence is observed in neutral buffers when an excess of complimentary oligonucleotide target is added. The BSK 39 has the following sequence: d((Fluoroscein) ACCGCTGCGTGAGCAGCGGU(dabsyl)CCTTGTCTTAGTCCAGAA) (SEQ ID NO:2).

The PCR reaction between the BSK 38 and BSK 39 primers and cloned HIV 1 control DNA was performed and monitored in an Idaho Lightcycler, Idaho Instruments Inc. Idaho Falls, Id. The reaction mixture of 20 mM Tris (ph 8.4), 50 mM KCl, 3 mM $MgCl_2$ 0.5 mg per mole bovine serum albumin (BSA) and 0.2 mM dNTP was added to 0.25 µM BSK 38 and 0.25 µM BSK 39 with 0.5 units of Taq (Takara) per 10 µl and 10 to $10^6$ molecules of cloned HIV 1 control DNA.

The reaction was set up by diluting the DNA polymerase 10 times with Idaho dilution buffer (10 mM Tris (pH 8.4) and 2.5 mg per ml BSA) to a concentration of 0.5 units per µl. The reaction cocktail was made with 0.25 mg/ml of BSA (final) and one half of the BSA was coming from the cocktail and one half from the DNA polymerase solution. The capillary tubes were filled as described in the Idaho Lightcycler manual. Cycling conditions of 4 minutes at 94 followed by 1 second at 94 then 15 seconds at 55 and 40 seconds at 74 before repeating the cycle.

Incorporation of oligonucleotides into the PCR product was monitored in real time using the Lightcycler and with the results shown in FIG. 1 where it can be seen that the number of cycles until fluorescence starts to be detected decreases with increasing concentration starting target DNA molecules. When the PCR reaction was stopped after an arbitrary amount of time and the reaction product separated and examined by electrophoresis it could be seen that the fluorescence increases with the increasing number of copies of the DNA target in proportion to the starting number of DNA target molecules and the cycle number. The sensitivity of the detection is comparable to that of regular PCR primers. Subsequent gel assays demonstrate that the fluorescent product of the expected size were synthesized.

EXAMPLE 5

Derivitization of the N4 Position of Cytosine with an Terminal Amino Linker for Attachment to a Quencher Dye

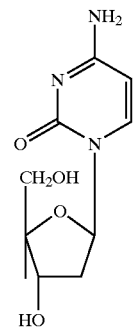

(IX)

To a round bottom flask containing the compound of formula (IX), diaminopropane is added along with $NaHSO_3$ in water at a pH of about 7.1 at 37° C. for about 5 to 7 days.

The product of formula (X)

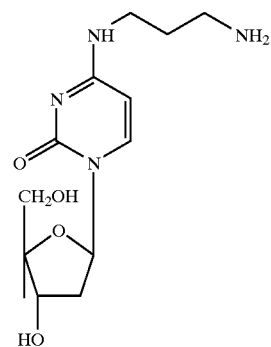

(X)

is formed which is purified by passing through a Dowex Ion Exchange resin column with a 0–5% $NH_4OH$ gradient and is subsequently dried under vacuum. The compound for formula (X) is reacted with trifluoroacetic anhydride in a pyridine/methanol solvent system to yield the compound of formula (XI).

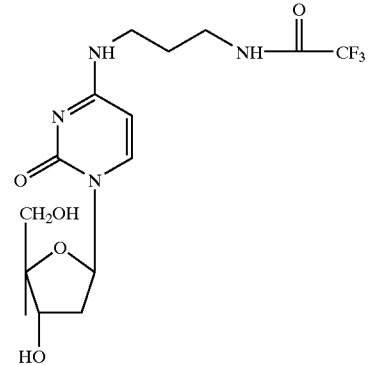

(XI)

The compound of formula (XI) is purified on a silica gel column with an eluant comprising 5–20% of ethyl acetate in methanol. Upon purification, the alcohol of the methanol moiety is protected by reacting the compound of formula (XI) with dimethoxytrityl chloride with triethylamine and pyridine to yield the compound of formula (XII).

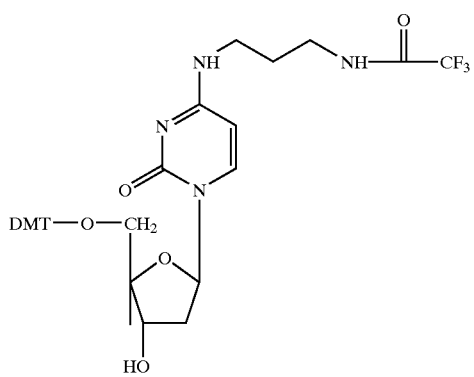

(XII)

The alcohol protected compound is purified by dissolving in methanol, vacuum drying and purifying on a silica gel column with an CHCl₃/methanol eluting system. The purified protected compound is reacted with methylamine in methanol at about 40° C. and subsequently dried to yield the compound of formula (XIII).

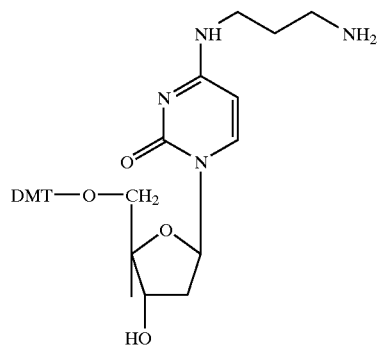

(XIII)

The compound of formula (XIII) can be reacted with any number of Q groups such as the succinimidyl esters, isothiocyanates, or sulfonyl chlorides such as DABSYL sulfonyl chloride, followed by subsequent conversion of the free hydroxyl to a phosphoramidate to yield a compound of formula (XIV):

EXAMPLE 6

Quencher Linkage to the C8 Position of a Purine

To a round bottom flask containing the compound of formula (XV), liquid bromine with water is added along with sodium acetate in water at a pH of about 5.0.

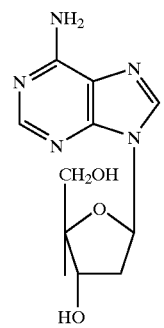

(XV)

The reaction mixture is heated until the reaction was complete and the compound of formula (XVI) is formed.

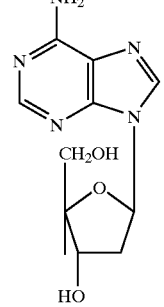

(XVI)

The compound of formula XVI is taken up in pyridine and cooled to 0° C. Trimethylchlorosilane is added drop-wise, followed by addition of benzylchloride. Following the addition of benzylchloride, water and NH₃ are added. The

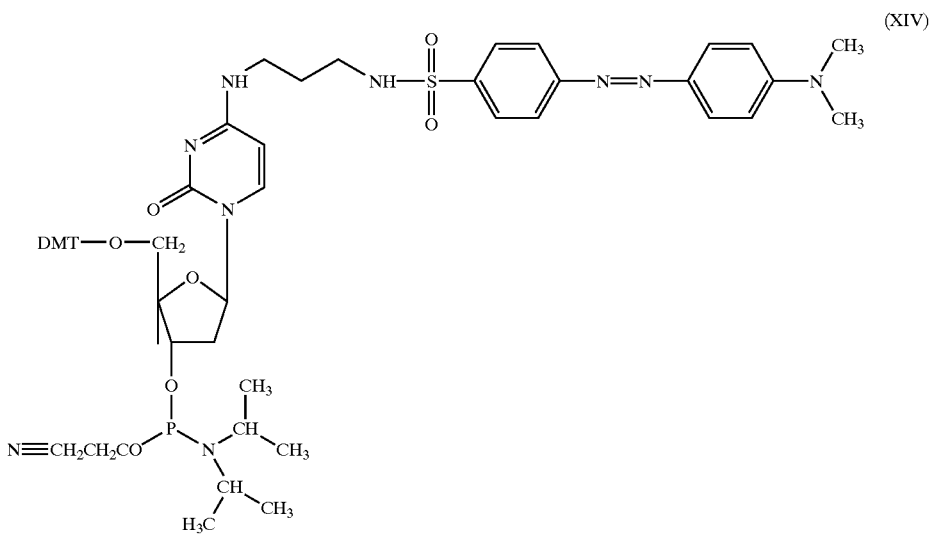

(XIV)

reaction mixture is dried and the product is extracted with ether. The compound of formula (XVII) is yielded.

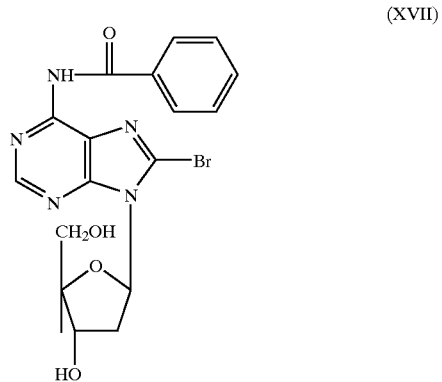

(XVII)

The alcohol of the methanol moiety is protected by reacting the compound of formula (XVII) with dimethoxytrityl chloride with triethylamine and pyridine to yield the compound of formula (XVIII). The compound is washed with sodium bicarbonate and purified by silica gel column chromatography. The compound of formula (XVII)) is refluxed with ethanol and diaminopropane and purified on a silica gel column to yield the compound of formula (XIX).

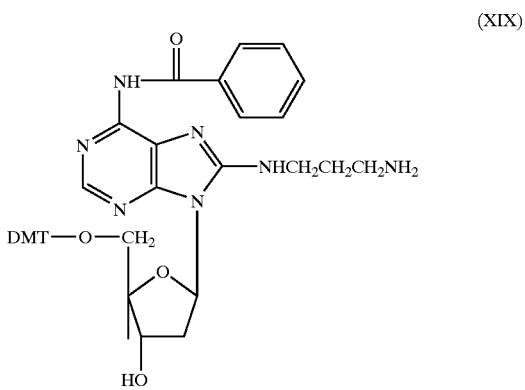

(XIX)

The protected alcohol can be reacted with any number of Q groups, for example DABSYL sulfonyl chloride in triethylamine and DMF, to yield the compound of formula (XX).

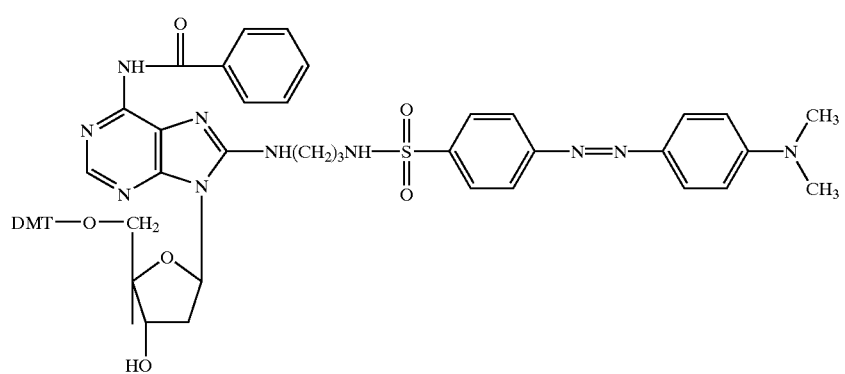

(XX)

The free hydroxyl is converted to the phosphoramidite such as described in example 5 to yield a compound of formula (XIX).

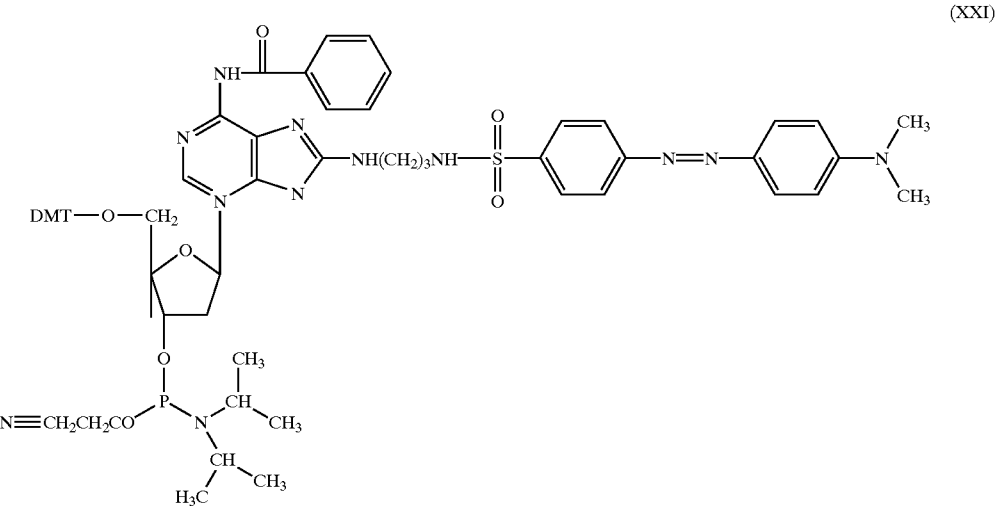

(XXI)

Although the invention has been described with reference to specific examples, it should be understood that various modifications can be made without departing from the spirit of the invention. Accordingly, the invention is to be limited only by the following claims.

We claim:

1. A derivatized pyrimidine or purine compound having the following structure:

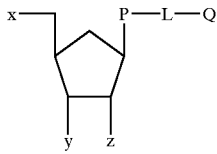

wherein, L is a linker group selected from the group consisting of —CH=CH—C(O)—NH—(CH$_2$)$_n$—NH—, —CH=CH—C(O)—NH—CH$_2$—CH$_2$(O—CH$_2$—CH$_2$)$_m$—NH—, —C C—C(O)—(CH$_2$)$_n$—NH—, —CH=CH—C(O)—NH—(CH$_2$)$_n$—CO$_2$—, —CH=CH—C(O)—NH—(CH$_2$)$_n$—NH—, —(CH$_2$)$_n$—NH—, and —NH—(CH$_2$)$_n$—NH—, wherein n is an integer from 2 to 12, and m is 1 or 2, and Q is a quencher group selected from the group consisting of radicals of azo dyes and triphenyl methane dyes;

P represents a pyrimidine selected from the group consisting of uridine, thymidine and cytosine or the purine adenine; substituted with a linker L at the 4 position, when P is a pyrimidine and at the 8 position when P is a purine;

wherein said pyrimidine is linked to the sugar at the 1-position nitrogen and said guanine is linked to the sugar at the 9-position nitrogen and either:

x is an activated phosphorus group capable of bonding to a 3'-hydroxyl group of a nucleotide or polynucleotide selected from the group consisting of HO—P(=O)(—OH)—O—, HO—P(=O)(—OH)—O—P(=O)(—OH)—O—, HO—P—(=O)(—OH)—O—P(=O)(—OH)—O—P(=O)(—OH)—O—, (HO)$_2$P(=S)—O—, (HO)$_2$P(=O)—O—(HO)P(=O)—O—(HO)P(=S)—O—, —O—P(OCH$_3$)(N(iso-propyl)$_2$), —O—P(OCH$_2$CH$_2$CN)(N(isopropyl)$_2$) and —O—P(CH$_3$)(N(iso-propyl)$_2$); or x is NH$_2$, H, OH or a protected hydroxyl; y is a protected hydroxyl group, OH, H or NH$_2$, and z is —H, —OH, —F, —OCH$_3$, —O-allyl, a protected hydroxyl group, —NH$_2$ or a protected amine group; or y is an activated phosphorus group capable of bonding to a 5' hydroxyl group of a nucleotide or polynucleotide selected from the group consisting of HO—P(=O)(—OH)—O—, HO—P(=O)(—OH)—O—P(=O)(—OH)—O—, HO—P—(=O)(—OH)—O—P(=O)(—OH)—O—P(=O)(—OH)—O—, (HO)$_2$P(=S)—O—, (HO)$_2$P(=O)—O—(HO)P(=O)—O—(HO)P(=S)—O—, —O—P(OCH$_3$)(N(iso-propyl)$_2$), —O—P(OCH$_2$CH$_2$CN)(N(isopropyl)$_2$) and —O—P(CH$_3$)(N(iso-propyl)$_2$); or y is NH$_2$, H, OH or a protected hydroxyl; x is a protected hydroxyl group, OH, H or NH$_2$, and z is —H, —OH, —F, —OCH$_3$, —O-allyl, a protected hydroxyl group, NH$_2$ or a protected amine group.

2. The compound of claim 1, wherein P is uridine, cytosine, or adenine.

3. The compound of claim 1, wherein L is —CH=CH—C(O)—NH—(CH$_2$)$_6$—NH—, —NH—(CH$_2$)$_3$—NH—, or —NH—(CH$_2$)$_3$—NH—.

4. The compound of claim 1, wherein said protected hydroxyl group is selected from the group consisting of —O-allyl, —O-benzyl, —O-dimethoxytrityl, —O-trityl, —O-propargyl, —O-silyl (wherein the silyl group is selected from the group consisting of trimethylsilyl, triisopropylsilyl and t-butyldimethylsilyl) and —O-acetyl.

5. The compound of claim 1, wherein z is H.

6. The compound of claim 4, wherein y is (HO)₂P(=S)—O— or x is (HO)₂P(=O)—O—(HO)P(=O)—O—(HO)P(=S)—O—.

7. The compound of claim 1, wherein Q is a radical of an azo dye.

8. The compound of claim 1, wherein the radical of the azo dye or triphenyl methane dye is acid alizarin violet N, acid black 24, acid blue 29, acid blue 92, acid blue 113, acid blue 120, blue 161, acid orange 8, acid orange 51, acid orange 74, acid red 1, acid red 4, acid red 8, acid red 37, acid red 40, acid red 88, acid red 97, acid red 106, acid red 151, acid red 183, acid violet 7, acid yellow 17, acid yellow 25, acid yellow 29, acid yellow 34, acid yellow 38, acid yellow 40, acid yellow 42, acid yellow 65, acid yellow 76, acid yellow 99, alizarin yellow 66, crocein orange G, alizarin blue black B, palatine chrome black 6BN, mordant black 3, basic red 29, basic blue 66, brilliant yellow chrysophine, chrysoldin, crystal scarlet, fast black K salt, fast corinth V salt, fast garnet GBC, fat brown B, fat brown RR, mordant blue 9, mordant brown 1, mordant brown 4, mordant brown 6, mordant brown 33, mordant brown 48, mordant orange 1, mordant orange 6, mordant orange 10, oil red E6N, orange 11, orange G, palatine chrome black 6BN, palatine fast yellow BLN, tropaeolin O, acid yellow 36, 4-dimethylamino-2-methylazobenzene, disperse orange 1, disperse orange 3, disperse orange 13, disperse orange 25, disperse red 1, disperse red 13, disperse red 19, disperse yellow 3, disperse yellow 5, disperse yellow 7, ethyl red, methyl red, naphthyl red, 4-phenylazoaniline, 4-phenylazomalcinanil, 4-phenylazophenol, 4(4-nitrophenylazo) resorcinol, nitro red, orange II, para red, Sudan I, Sudan II, Sudan III, Sudan IV, Sudan Orange G, or Sudan Red 7B.

9. The compound of claim 1, wherein the radical of the azo dye is acid alizarin violet N, acid black 24, acid blue 92, acid blue 113, acid blue 120, acid orange 8, acid orange 51, acid orange 74, acid red 1, acid red 4, acid red 8, acid red 88, acid red 151, acid red 183, acid yellow 34, acid yellow 40, acid yellow 76, crocein orange G, crystal scarlet, mordant blue 9, mordant brown 1, mordant brown 33, mordant orange 1, mordant orange 6, mordant orange 10, orange 11, orange G, palatine chrome black 6BN, palatine fast yellow BLN, tropaeolin O, 4-dimethylamino-2-methylazobenzene, ethyl red, methyl red, naphthyl red, 4-phenylazoaniline, 4-phenylazophenol, disperse orange 3, disperse orange 13, disperse orange 25, disperse yellow 7, orange 2, para red, Sudan I, Sudan II, Sudan III, or Sudan Orange G.

10. The compound of claim 1, wherein Q is a radical of a triphenyl methane dye.

11. The compound of claim 1, wherein the radical of the triphenyl methane dye is alkali blue 6B, aurintricarboxylic acid, basic violet 14, basic red 9, brilliant green, bromochlorophenyl blue, bromcresol purple, chlorophenol red, crystal violet, ethyl violet, fast green FCF, guinea green B, malachite green, methyl green, new fuchsia, pyrocatechol violet, thymol blue, thymophtalin, victoria blue B, victoria blue R, or victoria pure blue BO.

12. The compound of claim 11, wherein the triphenyl methane dye is linked to the linker through reaction with a dye containing an isocyanate group, an isothiocyanate group, or an N-succinimidyl ester group.

13. The compound of claim 11, wherein the radical of the triphenyl methane dye is malachite green.

14. The compound of claim 1, wherein Q is uniblue B, alizarin blue black B, alizarin red S, alizarin violet 3R, fast blue BB, or fast blue RR.

15. The compound of claim 1, wherein Q is

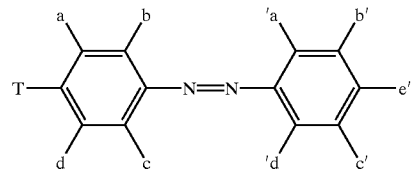

T is —NH—, —SO₂—, —O—, —S—, —C(O)—S—, —C(O)—, —C(O)—NH—, —C(O)—O—, —C(S)—NH—, or —C(S)—O—, a, a', b, b', c, c', d, d', and e' are each —H, —Cl, —Br, —F, —OCH₃, —OH, —CH₃, SO₃, diazophenyl, diazo-1-naphthyl, NO₂, —CO₂R, or —N(R)₂, and R is —H, —CH₃, or —CH₂—CH₃.

16. The compound of claim 15, wherein T is —SO₂—; a, a', b, b', c, c', d, and d' each are H; and e' is —N—(CH₃)₂ or —N—(CH₂—CH₃)₂.

17. The compound of claim 16, wherein e' is —N—(CH₃)₂.

18. The compound of claim 16, wherein e' is —N—(CH₂—CH₃)₂.

19. A method for producing a compound containing at least two nucleotides, wherein the method comprises linking the compound of claim 1 to another compound containing at least one nucleotide.

20. The method of claim 19, wherein the compound containing at least two nucleotides is an oligonucleotide.

* * * * *

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 1
ataatccacc ctatcccagt aggagaaat                                    29

<210> SEQ ID NO 2
<211> LENGTH: 38
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<223> OTHER INFORMATION: Description of Artificial Sequence: Synthetic
      oligonucleotide

<400> SEQUENCE: 2
accgctgcgt gagcagcggu ccttgtctta gtccagaa                          38